US011877760B2

(12) United States Patent
Singh

(10) Patent No.: US 11,877,760 B2
(45) Date of Patent: Jan. 23, 2024

(54) ULTRASONIC SYSTEM AND METHODS

(71) Applicant: C. R. Bard, Inc., Franklin Lakes, NJ (US)

(72) Inventor: Aseem Singh, Tempe, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 608 days.

(21) Appl. No.: 17/254,005

(22) PCT Filed: Jul. 31, 2018

(86) PCT No.: PCT/US2018/044489
§ 371 (c)(1),
(2) Date: Dec. 18, 2020

(87) PCT Pub. No.: WO2020/027787
PCT Pub. Date: Feb. 6, 2020

(65) Prior Publication Data

US 2021/0251644 A1 Aug. 19, 2021

(51) Int. Cl.
*A61B 17/22* (2006.01)
*A61B 17/00* (2006.01)

(52) U.S. Cl.
CPC .................... *A61B 17/2202* (2013.01); *A61B 2017/00017* (2013.01)

(58) Field of Classification Search
CPC .......... A61B 17/22012; A61B 17/2202; A61B 17/320068; A61B 2017/00017;
(Continued)

(56) References Cited

U.S. PATENT DOCUMENTS 5,447,509 A 9/1995 Mills et al.
6,569,109 B2 5/2003 Sakurai et al.
(Continued)

FOREIGN PATENT DOCUMENTS

JP 2008539935 A 11/2008
JP 2017192743 A 10/2017
(Continued)

OTHER PUBLICATIONS

Office Action dated Apr. 28, 2022, pertaining to Japanese Patent Application 2020-572657.
(Continued)

*Primary Examiner* — Ryan J. Severson
(74) *Attorney, Agent, or Firm* — Dinsmore & Shohl LLP

(57) ABSTRACT

A system and method for operating an ultrasonic treatment device includes generating an ultrasound electrical signal using an ultrasound signal generator; supplying the ultrasound electrical signal to an ultrasonic transducer to generate ultrasonic vibratory motion of an ultrasonic vibration transmission member; monitoring an electrical characteristic associated with the ultrasonic transducer; processing the monitored electrical characteristic to determine at least one of a type of material encountered by a distal end of the ultrasonic vibration transmission member and a type of vascular pathway that the ultrasonic catheter is traversing; and controlling at least one of a modulation frequency and a waveform of the ultrasound electrical signal based on the determined at least one of the type material encountered by the distal end of the ultrasonic vibration transmission member and the type of vascular pathway that the ultrasonic catheter is traversing.

18 Claims, 7 Drawing Sheets

(58) Field of Classification Search
CPC ........... A61B 2017/22014; A61B 2017/22027; A61B 8/085
See application file for complete search history.

(56) References Cited

U.S. PATENT DOCUMENTS 6,761,690 B2 7/2004 Sakurai et al.
7,270,646 B2 9/2007 Sakurai et al.
7,819,826 B2 10/2010 Diederich et al.
8,118,742 B2 * 2/2012 Dickinson ............. B06B 1/0622 600/463
8,295,908 B2 * 10/2012 Carmeli ........... A61B 17/22012 600/407
8,345,512 B2 * 1/2013 Adachi ................. B06B 1/0292 367/181
8,845,537 B2 9/2014 Tanaka et al.
8,858,439 B2 10/2014 Tanaka et al.
9,022,935 B2 5/2015 Akagane
9,622,749 B2 4/2017 Vaitekunas et al.
9,750,523 B2 9/2017 Tsubuku
10,004,888 B2 * 6/2018 Chapelon .......... A61M 37/0092
10,043,965 B2 * 8/2018 Jo ......................... B06B 1/0215
11,033,292 B2 * 6/2021 Green ............ A61B 17/320068
2001/0039389 A1 * 11/2001 Sakurai ................. B06B 1/0253 601/2
2003/0199793 A1 * 10/2003 Sakurai ................. B06B 1/0253 601/2
2003/0225331 A1 * 12/2003 Diederich .............. A61B 18/04 600/437
2004/0162509 A1 * 8/2004 Sakurai ................. B06B 1/0253 601/2
2006/0052707 A1 * 3/2006 Dickinson ........... G01S 15/8915 600/466
2008/0269614 A1 * 10/2008 Adachi .............. G01N 29/2406 310/317
2009/0209900 A1 8/2009 Carmeli et al.
2010/0312107 A1 * 12/2010 Tanaka ................ A61B 18/148 600/439
2010/0312111 A1 * 12/2010 Tanaka ........... A61B 17/320092 600/443
2014/0288465 A1 * 9/2014 Akagane ........ A61B 17/320068 601/2
2014/0354111 A1 12/2014 Jo et al.
2015/0141734 A1 5/2015 Chapelon et al.
2016/0317178 A1 11/2016 Green et al.
2016/0325311 A1 * 11/2016 Vaitekunas ...... A61B 17/22012
2016/0331399 A1 * 11/2016 Tsubuku ........ A61B 17/320092
2021/0251644 A1 * 8/2021 Singh ..................... A61B 8/085
2022/0313293 A1 * 10/2022 Singh ............... A61B 17/22012
2023/0172624 A1 * 6/2023 Singh ................. A61B 17/2202 606/159

FOREIGN PATENT DOCUMENTS

KR 20130017878 A 2/2013
KR 1020130017878 A 2/2013
WO 2006120674 A1 11/2006

OTHER PUBLICATIONS

Communication under Rule 71(3) EPC dated Jan. 27, 2023, pertaining to EP Publication 3829461.

* cited by examiner

ULTRASONIC SYSTEM AND METHODS

CROSS-REFERENCE TO RELATED APPLICATIONS

This application is a U.S. national phase of International Application No. PCT/US2018/044489, filed Jul. 31, 2018, which is incorporated herein by reference in its entirety.

TECHNICAL FIELD

The present invention relates to an ultrasonic system and methods, and, more particularly, to a method for operating and/or determining an operational state of an ultrasonic treatment device of an ultrasonic system.

BACKGROUND ART

During the use of a typical ultrasonic treatment device, there is little or no control or knowledge of the procedural effects of the ultrasonic treatment device in real time. For example, the physician typically will place the ultrasonic catheter portion of the ultrasonic treatment device over a guidewire and then move the distal end into contact with the occlusion without any feedback as to the type of material being encountered by the distal end of the ultrasonic vibration transmission member of the ultrasonic catheter and/or a type of vascular pathway that the ultrasonic catheter is traversing.

What is needed in the art is a method for operating, and/or determining an operational state of, an ultrasonic treatment device, in which at least one of a type material encountered by a distal end of an ultrasonic vibration transmission member of an ultrasonic catheter and a type of vascular pathway that the ultrasonic catheter is traversing is determined and acted upon in real time.

SUMMARY OF INVENTION

The present invention provides a system and methods in which one or more electrical characteristics of an ultrasonic transducer is monitored to determine at least one of a type material encountered by a distal end of an ultrasonic vibration transmission member of an ultrasonic catheter and a type of vascular pathway that the ultrasonic catheter is traversing. The determination may then be used to control a frequency and/or a waveform of the ultrasound electrical signal to maintain stable operation of the ultrasonic treatment device and/or a result of the determination may be displayed at a display screen of a user interface.

The invention in one form is directed to an ultrasonic system that includes an ultrasound signal generator configured to generate an ultrasound electrical signal. An ultrasonic treatment device is electrically coupled the ultrasound signal generator. The ultrasonic treatment device has an ultrasonic transducer drivably coupled to an ultrasonic vibration transmission member of an ultrasonic catheter. The ultrasonic transducer receives the ultrasound electrical signal to generate an ultrasonic vibratory motion of the ultrasonic vibration transmission member. Circuitry is configured to monitor an electrical characteristic associated with the ultrasonic transducer. The electrical characteristic may be one of a total voltage across the ultrasonic transducer, a total current to the ultrasonic transducer, an induced current of the ultrasonic transducer, or a Power Factor between the total voltage and the total current. The circuitry includes a processor circuit configured to process the monitored electrical characteristic to determine at least one of a type of material encountered by a distal end of the ultrasonic vibration transmission member and a type of vascular pathway that the ultrasonic catheter is traversing. The circuitry is configured to generate a control signal that is supplied to the ultrasound signal generator to control at least one of a modulation frequency and a waveform of the ultrasound electrical signal based on the determined at least one of the type material encountered by the distal end of the ultrasonic vibration transmission member and the type of vascular pathway that the ultrasonic catheter is traversing.

The invention in another form is directed to a method for operating an ultrasonic treatment device having an ultrasonic transducer drivably coupled to an ultrasonic vibration transmission member of an ultrasonic catheter. The method includes generating an ultrasound electrical signal using an ultrasound signal generator; supplying the ultrasound electrical signal to the ultrasonic transducer to generate ultrasonic vibratory motion of the ultrasonic vibration transmission member; monitoring an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current; processing the monitored electrical characteristic to determine at least one of a type of material encountered by a distal end of the ultrasonic vibration transmission member and a type of vascular pathway that the ultrasonic catheter is traversing; and controlling at least one of a modulation frequency and a waveform of the ultrasound electrical signal based on the determined at least one of the type material encountered by the distal end of the ultrasonic vibration transmission member and the type of vascular pathway that the ultrasonic catheter is traversing.

The invention in another form is directed to a method of determining an operational state of an ultrasonic treatment device having an ultrasonic transducer drivably coupled to an ultrasonic vibration transmission member of an ultrasonic catheter. The method includes exciting the ultrasonic transducer with an ultrasound electrical signal using an ultrasound signal generator to generate ultrasonic vibratory motion of the ultrasonic vibration transmission member; monitoring an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current; processing the monitored electrical characteristic to determine at least one of a material encountered by a distal end of the ultrasonic vibration transmission member and a type of vascular pathway that the ultrasonic catheter is traversing; and displaying a result of the processing step at a display screen of a user interface, the result including at least one of the type of material encountered by the distal end of the ultrasonic vibration transmission member and the type of vascular pathway that the ultrasonic catheter is traversing.

An advantage of the present invention is that at least one of a type material encountered by a distal end of an ultrasonic vibration transmission member of an ultrasonic catheter and a type of vascular pathway that the ultrasonic catheter is traversing is determined and may be acted upon in real time during an atherectomy procedure. For example, the determination may be used to automatically adjust a frequency and/or a waveform of the ultrasound electrical signal so as to maintain stable operation of the ultrasonic treatment device. Alternatively, or in addition to the automatic control, a result of the determination may be displayed to the physician during the atherectomy procedure, and the physician may adjust the atherectomy technique based on the displayed result. Also, in a system that does not utilize automatic control, the displayed result may be used by the physician to manually adjust operational parameters of the ultrasound signal generator.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DESCRIPTION OF EMBODIMENTS

Figure 1:
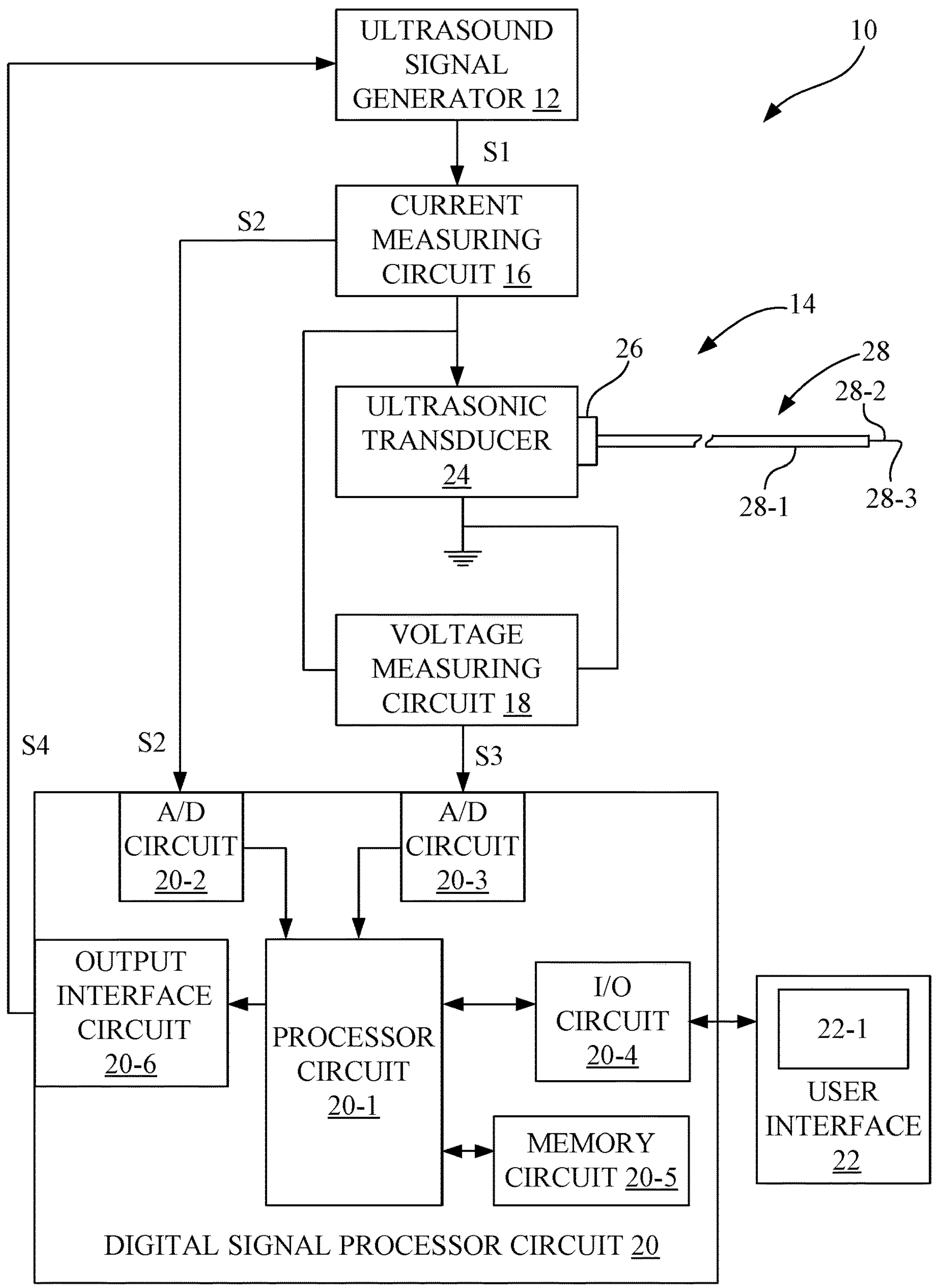
FIG. 1 is a block diagram of an ultrasonic system in accordance with an aspect of the present invention.

Referring now to the drawings, and more particularly to FIG. 1, there is shown a block diagram of an ultrasonic system 10, which may be used in atherectomy procedures. Ultrasonic system 10 includes an ultrasound signal generator 12, an ultrasonic treatment device 14, a current measuring circuit 16, a voltage measuring circuit 18, a digital signal processor circuit 20, and a user interface 22.

Ultrasonic treatment device 14 includes an ultrasonic transducer 24, a sonic coupler 26, and an ultrasonic catheter 28. Ultrasonic catheter 28 may be configured as a single use disposable device, and may include sonic coupler 26 integral therewith. Ultrasonic transducer 24 may be part of a reusable handpiece. Alternatively, ultrasonic treatment device 14 may be a unitary disposable assembly. Ultrasonic catheter 28 includes a sheath 28-1 and an ultrasonic vibration transmission member 28-2 having a distal end 28-3. Ultrasonic vibration transmission member 28-2, e.g., a corewire, is connected to ultrasonic transducer 24 via sonic coupler 26.

Ultrasound signal generator 12 may be, for example, a CROSSER® brand generator available from C. R. Bard., Inc. Ultrasonic transducer 24 may be the transducer located in the CROSSER® brand handpiece used with the CROSSER® brand generator. Ultrasonic catheter 28 may be, for example, a CROSSER® brand chronic total occlusion (CTO) ultrasonic catheter available from C. R. Bard., Inc.

During operation, ultrasound signal generator 12 generates an ultrasound electrical signal S1 in the ultrasound frequency spectrum, and may be in an operating frequency range of, for example, 18 kilohertz (kHz) to 40 kHz, and more preferably, is initially set at 20 kHz. Ultrasound electrical signal S1 has a predetermined waveform, e.g., sinusoidal or square wave, and has a variable duty cycle. The duty cycle may be, for example, initially 50 percent, and may be varied to adjust the on and off time of ultrasound electrical signal S1.

Ultrasound electrical signal S1 is supplied to ultrasonic transducer 24 to excite ultrasonic transducer 24 to generate ultrasonic vibratory motion, as is known in the art. The ultrasonic vibratory motion is transferred to ultrasonic vibration transmission member 28-2 of ultrasonic catheter 28 via sonic coupler 26.

Current measuring circuit 16 is interposed between ultrasound signal generator 12 and ultrasonic transducer 24, so as to measure a total current being supplied to ultrasonic transducer 24. Current measuring circuit 16 may include, for example, a sensing transformer for sensing the total current supplied to ultrasonic transducer 24. Current measuring circuit 16 generates a total current signal S2, which is supplied to digital signal processor circuit 20.

Voltage measuring circuit 18 is connected, e.g., to both the input and ground sides across ultrasonic transducer 24, so as to measure a total voltage drop across ultrasonic transducer 24. Voltage measuring circuit 18 may include, for example, a voltmeter for sensing the total voltage across ultrasonic transducer 24. Voltage measuring circuit 18 generates a total voltage signal S3, which is supplied to digital signal processor circuit 20.

Digital signal processor circuit 20 may be formed as one or more Application Specific Integrated Circuits (ASIC). In the present embodiment, digital signal processor circuit 20 includes a processor circuit 20-1, an analog-to-digital (A/D) converter circuit 20-2, an analog-to-digital (A/D) converter circuit 20-3, an input/output (I/O) circuit 20-4, a memory circuit 20-5, and an output interface circuit 20-6.

Processor circuit 20-1 is electrically and communicatively coupled, e.g., through an internal electrical bus and support circuitry, to each of A/D converter circuit 20-2, A/D converter circuit 20-3, I/O circuit 20-4, memory circuit 20-5, and output interface circuit 20-6. Processor circuit 20-1 may include one or more programmable microprocessors and associated circuitry, such as an input/output interface, clock, buffers, memory, etc. Processor circuit 20-1 may be programmed, e.g., through software or firmware stored in memory circuit 20-5, to execute program instructions to process received input data, and to generate and send output data.

A/D converter circuit 20-2 converts the analog total current signal S2 into a corresponding digital representation that is supplied to processor circuit 20-1 for processing. Likewise, A/D converter circuit 20-3 converts the analog total voltage signal S3 into a corresponding digital representation that is supplied to processor circuit 20-1 for processing.

User interface 22 may be electrically and communicatively coupled, e.g., through a multi-wire cable or USB, to I/O circuit 20-4. Alternatively, user interface 22 may be a wireless link, e.g., Bluetooth, which is communicatively coupled to I/O circuit 20-4. User interface 22 may be, for example, a touch screen device, a computer, tablet, or a smart phone. User interface 22 is configured to send user input commands to digital signal processor circuit 20, and is configured to receive output information from digital signal processor circuit 20 for display on a display screen 22-1 of user interface 22. Display screen 22-1 may be, for example, one of a liquid crystal display (LCD) or a light-emitting diode (LED) display.

Memory circuit 20-5 is an electronic non-transitory memory having a plurality of data storage locations, as is well known in the art. Memory circuit 20-5 may include one or more of volatile memory circuits, such as random access memory (RAM), and non-volatile memory circuits, such as read only memory (ROM), electronically erasable programmable ROM (EEPROM), NOR flash memory, NAND flash memory, etc.

Output interface circuit 20-6 is electrically and communicatively coupled, e.g., through a multi-wire cable or USB, to a control input of ultrasound signal generator 12. Alternatively, output interface circuit 20-6 may be a wireless link, e.g., Bluetooth, which is communicatively coupled to ultrasound signal generator 12. Output interface circuit 20-6 receives control signals from processor circuit 20-1, and conditions the control signals (e.g., analog-to-digital conversion, signal amplification, etc.), as appropriate, to generate an output control signal S4 to be received by ultrasound signal generator 12.

In the present embodiment, processor circuit 20-1 executes program instructions to process the digital representation of the total current signal S2 supplied by A/D converter circuit 20-2 and the digital representation of the total voltage signal S3 supplied by A/D converter circuit 20-3. The program instructions may include, for example, program steps to calculate a Power Factor between the total current signal S2 and total voltage signal S3, and may include program steps to calculate an induced (motion) current of, e.g., generated by, ultrasonic transducer 24. The program instructions may include algebraic functions, comparison functions, gain control functions, phase lock loop functions, and/or zero crossing calculation functions, as appropriate, to calculate the Power Factor and/or induced current of ultrasonic transducer 24.

Figure 2:
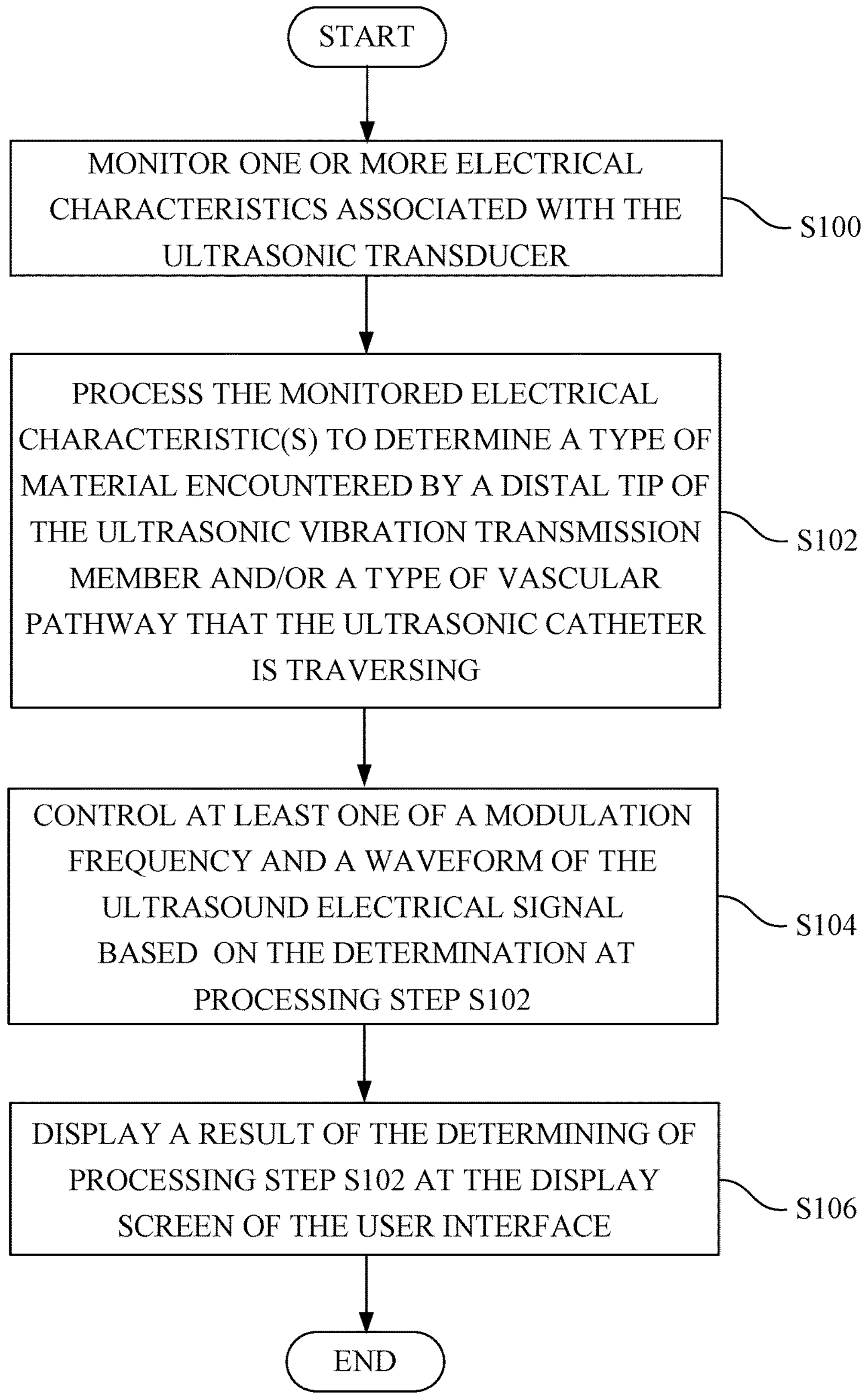
FIG. 2 is a general flowchart of a method for operating, and/or determining an operational state of, an ultrasonic treatment device of the ultrasonic system of FIG. 1.

Referring also to FIG. 2, there is depicted a general flowchart of a method for operating, and/or determining an operational state of, ultrasonic treatment device 14. Each of the steps of the flowchart of FIG. 2 may be effected as program instructs that are executed by processor circuit 20-1, in conjunction with the total voltage across ultrasonic transducer 24 as indicated by the digital representation (output of A/D converter circuit 20-3) of the total voltage signal S3 generated by voltage measuring circuit 18 and/or the total current supplied to ultrasonic transducer 24 as indicated by the digital representation (output of A/D converter circuit 20-2) of the total current signal S2 generated by current measuring circuit 16.

Referring to step S100 of FIG. 2, one or more electrical characteristics associated with ultrasonic transducer 24 is monitored. In the present embodiment, digital signal processor circuit 20 monitors at least one electrical characteristic associated with ultrasonic transducer 24, based on inputs received from current measuring circuit 16 and/or voltage measuring circuit 18. The electrical characteristic(s) may be one or more of the total voltage across ultrasonic transducer 24 as indicated by the digital representation of the total voltage signal S3, a total current to ultrasonic transducer 24 as indicated by the digital representation of the total current signal S2, an induced current of ultrasonic transducer 24 as calculated using program instructions executed by processor circuit 20-1, or a Power Factor between the total voltage and the total current, as calculated using program instructions executed by processor circuit 20-1.

At step S102, the monitored electrical characteristic(s) is/are processed to determine a type of material encountered by distal end 28-3 of ultrasonic vibration transmission member 28-2 and/or a type of vascular pathway that ultrasonic catheter 28 is traversing. For example, in the present embodiment, processor circuit 20-1 processes the monitored electrical characteristic(s) to determine at least one of a type of material encountered by a distal end 28-3 of ultrasonic vibration transmission member 28-2 and a type of vascular pathway that ultrasonic catheter 28 is traversing. The processing step is performed by processor 20-1 and includes comparing each monitored electrical characteristic to a respective threshold (single point data) and/or a data profile (multi-point data over time) to determine the type of material encountered by distal end 28-3 of ultrasonic vibration transmission member 28-2. Each respective threshold and/or data profile of a plurality of thresholds and/or data profiles may be represented as digital numerical values, and stored in memory circuit 20-5 for access by processor circuit 20-1.

For example, the total voltage across ultrasonic transducer 24, as indicated by the digital representation of the total voltage signal S3, may be compared to a total voltage threshold and/or total voltage data profile. The total current to ultrasonic transducer 24, as indicated by the digital representation of the total current signal S2, may be compared to a total current threshold and/or a total current data profile. The induced current of ultrasonic transducer 24, as calculated using the program instructions executed by processor circuit 20-1, may be compared to an induced current threshold and/or data profile. The Power Factor between the total voltage and the total current, as calculated using the program instructions executed by processor circuit 20-1, may be compared to a Power Factor threshold and/or Power Factor data profile.

At step S104, at least one of a modulation frequency and a waveform of ultrasound electrical signal S1 is controlled based on the determination at processing step S102. Initially, for example, the base frequency for ultrasound electrical signal S1 may be 20 kHz, and the modulation frequency may be, e.g., 10 Hz. As an example, the amount of change in the modulation frequency may be in a range of plus or minus 100 percent, i.e., in a range of 0 Hz-20 Hz.

In the present embodiment, as a result of the processing at step S102, processor circuit 20-1 may generate a control signal that is conditioned by output interface circuit 20-6 and supplied as output control signal S4 to ultrasound signal generator 12. Output control signal S4 is received by ultrasound signal generator 12 to control at least one of the modulation frequency and a waveform (e.g., duty cycle) of ultrasound electrical signal S1 based on the determined type material encountered by the distal end 28-3 of ultrasonic vibration transmission member 28-2 of ultrasonic catheter 28, and/or the type of vascular pathway (e.g., bend, tortuous, straight, etc.) that ultrasonic catheter 28 is traversing, so as to maintain ultrasonic treatment device 14, and in particular, ultrasonic catheter 28, in a stable operating condition and to reduce the risk of breakage of ultrasound vibration transmission member 28-2.

At step S106, a result of the determining of processing step S102 may be displayed at display screen 22-1 of user interface 22. It is contemplated that step S106 may be supplemental to, or in lieu of, step S104.

In the present embodiment, at step S106, a result of the processing performed by processor circuit 20-1 (see step S102) may be displayed at display screen 22-1 of user interface 22. The result may be in textual form, pictorial form, graphical form, or a combination thereof. The result to be displayed may include an identification of prolapsing, an identification of the type of material being encountered by distal end 28-3 of ultrasonic vibration transmission member 28-2 and/or the type of vascular pathway that ultrasonic catheter 28 is traversing, e.g., the tortuosity of the vascular pathway.

In addition, supplemental to steps S100-S106, each monitored electrical characteristic may be monitored over a period of time, e.g., 0.5 to 1 second, to detect a change in value over time to determine a progress of advancement of ultrasonic vibration transmission member 28-2 of ultrasonic catheter 28 through a vascular obstruction (e.g., lesion or plaque) in the vascular pathway into which ultrasonic catheter 28 is deployed. The progress of advancement of ultrasonic vibration transmission member 28-2 of ultrasonic catheter 28 through the vascular obstruction in the vascular pathway may be represented graphically on display screen 22-1 of user interface 22.

FIGS. 3-6 depict how empirical data may be used to determine appropriate thresholds and/or operation profiles to signify the occurrence of various atherectomy events. In each of FIG. 3-6, the vertical axis is in units of Volts, and the horizontal axis is in arbitrary time units, unless otherwise specified. In each of FIGS. 3-6, actual data points are represented by dots, and the rectangles represent a range of voltages associated with the data point groupings. The data was collected using the CROSSER® ultrasonic catheter system and using a CROSSER® brand chronic total occlusion (CTO) ultrasonic catheter, model CR14S catheter, available from C. R. Bard., Inc.

Figure 3:
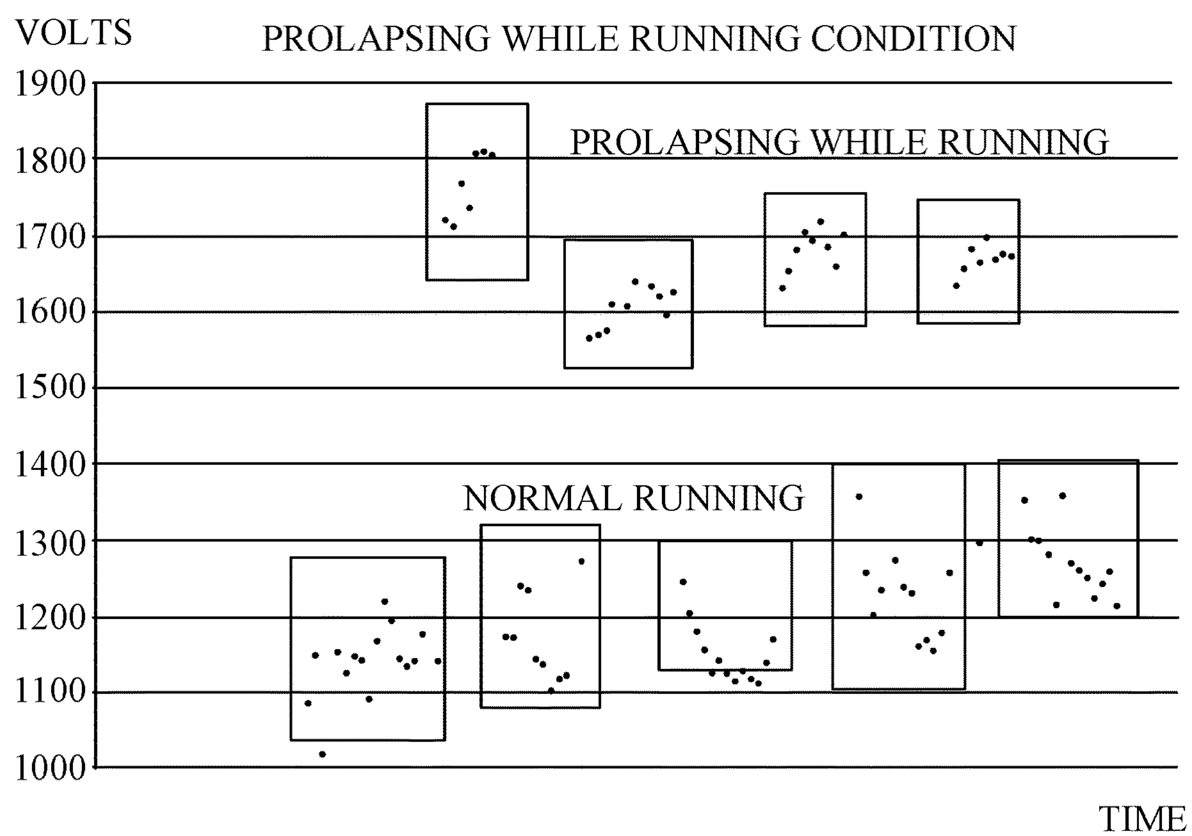
FIG. 3 is a graph that depicts a "prolapsing while running" condition for determining a threshold and/or data profile for use in detecting a prolapse condition.
Figure 4:
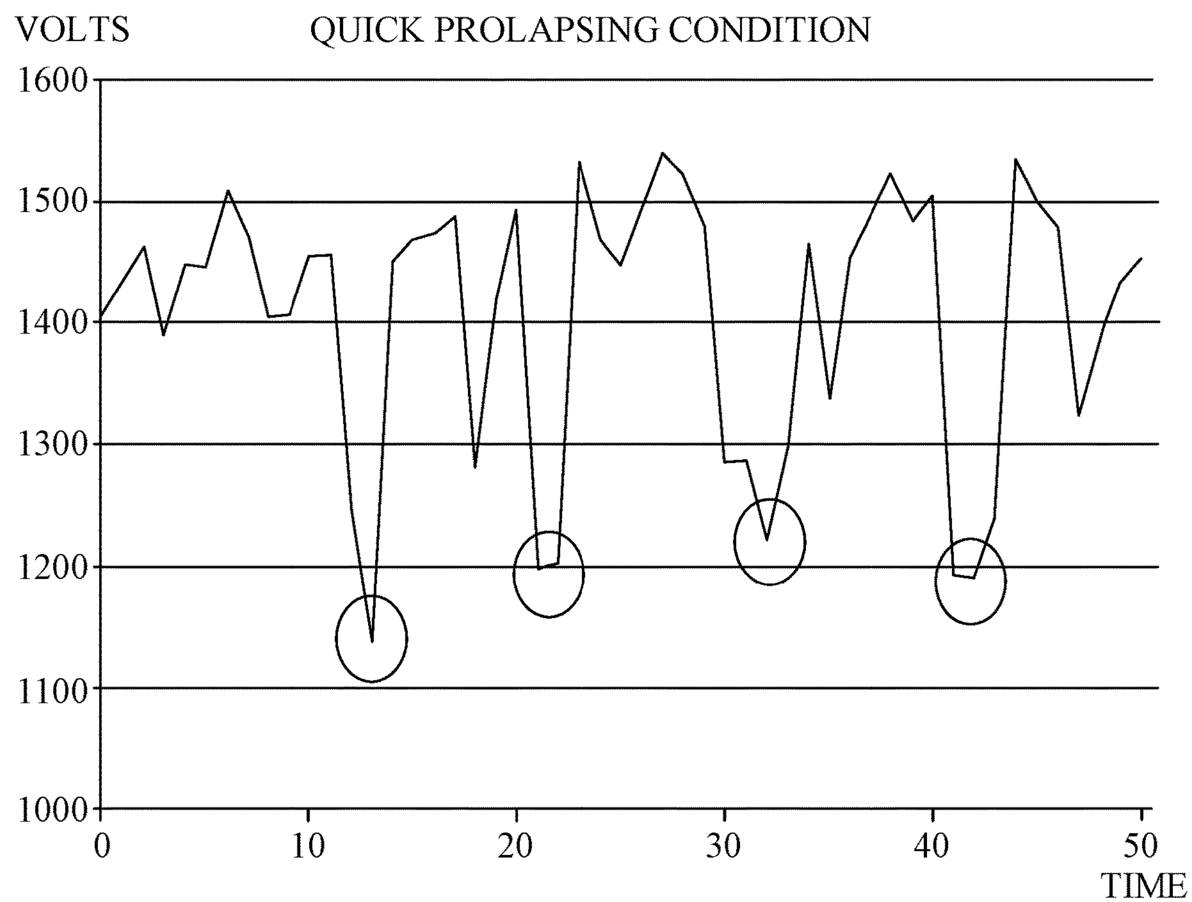
FIG. 4 is a graph that depicts a "quick prolapsing" condition within a prolapse event of the graph of FIG. 3.
Figure 5:
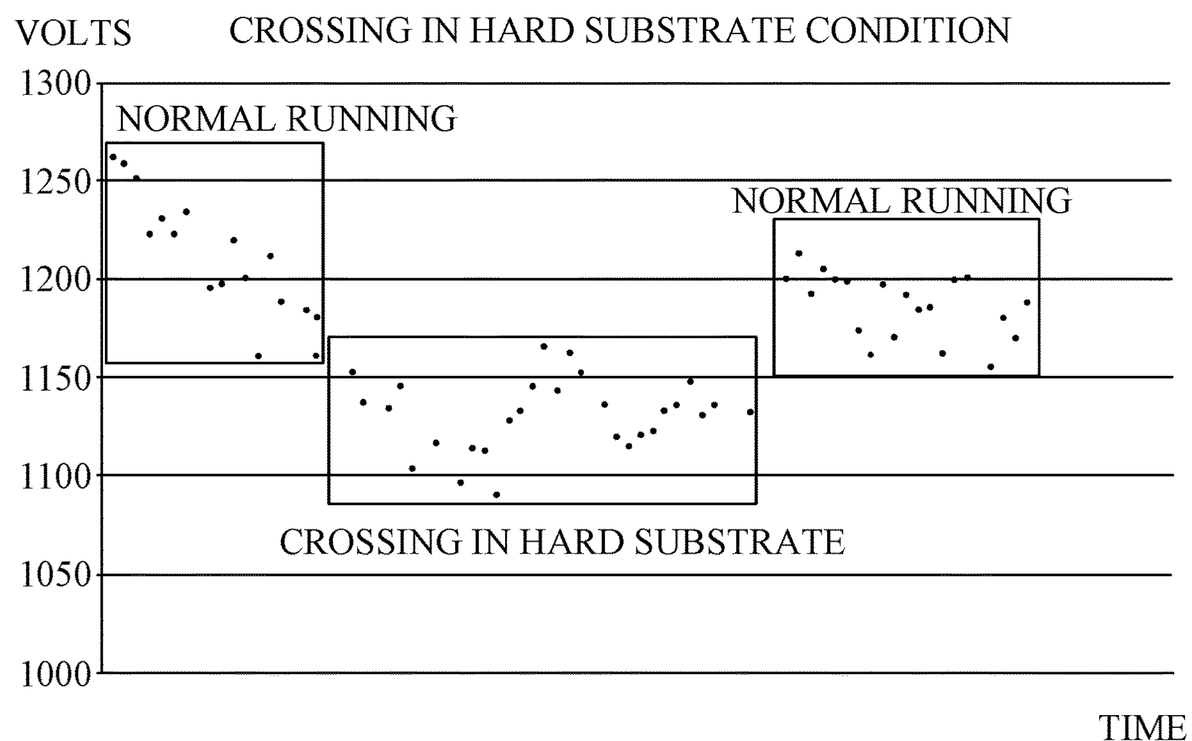
FIG. 5 is a graph that depicts a "crossing in hard substrate" condition, for determining a threshold and/or data profile for use in detecting hard substrate engagement and crossing.

Also, for each of the graphs of FIGS. 3-5, ultrasound signal generator 12 was set to run with the following parameter set: automatic gain control (AGC) 900, frequency of 20 kHz with 10 Hz modulation and 50 percent duty cycle, and start phase is 1500 volts. For the graphs of FIG. 6, ultrasound signal generator 12 was set to run with the following parameter set: automatic gain control (AGC) 700, frequency of 20 kHz with 17 Hz modulation and 50 percent duty cycle, and start phase is 1600 volts. For the graph of FIG. 7, ultrasound signal generator 12 was set to run with the following parameter set: automatic gain control (AGC) 700, frequency of 20 kHz with 10 Hz modulation and 50 percent duty cycle, and start phase is 1600 volts. In describing the various graphs of FIGS. 3-6, the term "normal running" means operation of the ultrasonic catheter 28 in the vascular pathway prior to engagement with a vascular occlusion in the vascular pathway.

The graph of FIG. 3 is directed to detecting the event of a prolapse while running. As used herein, the term "prolapse" is the condition wherein distal end 28-3 of ultrasonic vibration transmission member 28-2 is pressed against the vascular occlusion (e.g., plaque or lesion) and the ultrasonic vibration transmission member 28-2 begins to bend, which can lead to breakage. Empirical data was collected during normal running conditions, and with prolapse during running. The graph of FIG. 3 may form the basis for determining a threshold value (single point data), or alternatively profile data (multi-point data over time indicative of the condition), for comparison the digital representation of the total voltage signal S3, in real time, to determine whether a prolapse while running is detected. The threshold, or alternatively the profile data, may be stored in memory circuit 20-5 for retrieval and use by processor circuit 20-1 in making the comparison.

For example, according to the graph, a total voltage measured by voltage measuring circuit 18 below 1400 would indicate that ultrasonic treatment device 14 is in a normal running state, and a value above 1500 volts would indicate that ultrasonic treatment device 14 is in a prolapsed running state. Accordingly, a total voltage threshold for comparison to the digital representation of the total voltage signal S3 (voltage across ultrasonic transducer 24) to indicate a "prolapse while running" condition may be selected in the range 1400 to 1500 volts, depending on the amount of overshoot or undershoot to be allowed. Output control signal S4 may then be adjusted to prevent the prolapse from becoming destructive to ultrasonic vibration transmission member 28-2.

The graph of FIG. 4 is directed to the event of a quick prolapsing during one of the "prolapse while running" events of FIG. 3, and is shown at a higher resolution. It is noted that a quick undulation across the total voltage threshold will indicate a quick prolapse condition.

The graph of FIG. 5 is directed to the events of detecting a hard substrate, and detecting the engagement with and/or crossing of the hard substrate, e.g., calcified plaque in a vascular pathway. Empirical data was collected during normal running conditions, and during engagement and crossing of a hard substrate. The graph of FIG. 5 may form the basis for determining a threshold value (single point data), or alternatively profile data (multi-point data over time indicative of the condition), for comparison the digital representation of the total voltage signal S3, in real time, to detect a hard substrate, detect the engagement with the hard substrate, and/or detect crossing of the hard substrate. The threshold, or alternatively the profile data, may be stored in memory circuit 20-5 for retrieval and use by processor circuit 20-1 in making the comparison, and for adjusting output control signal S4 to prevent prolapse.

For example, according to the graph, a total voltage measured by voltage measuring circuit 18 below 1150 volts may be used as a total voltage threshold in a crossing state to indicate a transition of operation of ultrasonic treatment device 14 from a normal running state to engagement with a hard substrate crossing state. If the procedure remains below the total voltage threshold for a predetermined amount of time, then the determination can be made that distal end 28-3 of ultrasonic vibration transmission member 28-2 is in the process of crossing the hard substrate, i.e., is in a "crossing in hard substrate" condition. Accordingly, the total voltage threshold for comparison to the total voltage across ultrasonic transducer 24 to indicate a hard substrate crossing condition may be selected to be 1150 volts, depending on the amount of overshoot or undershoot to be permitted.

Figure 6:
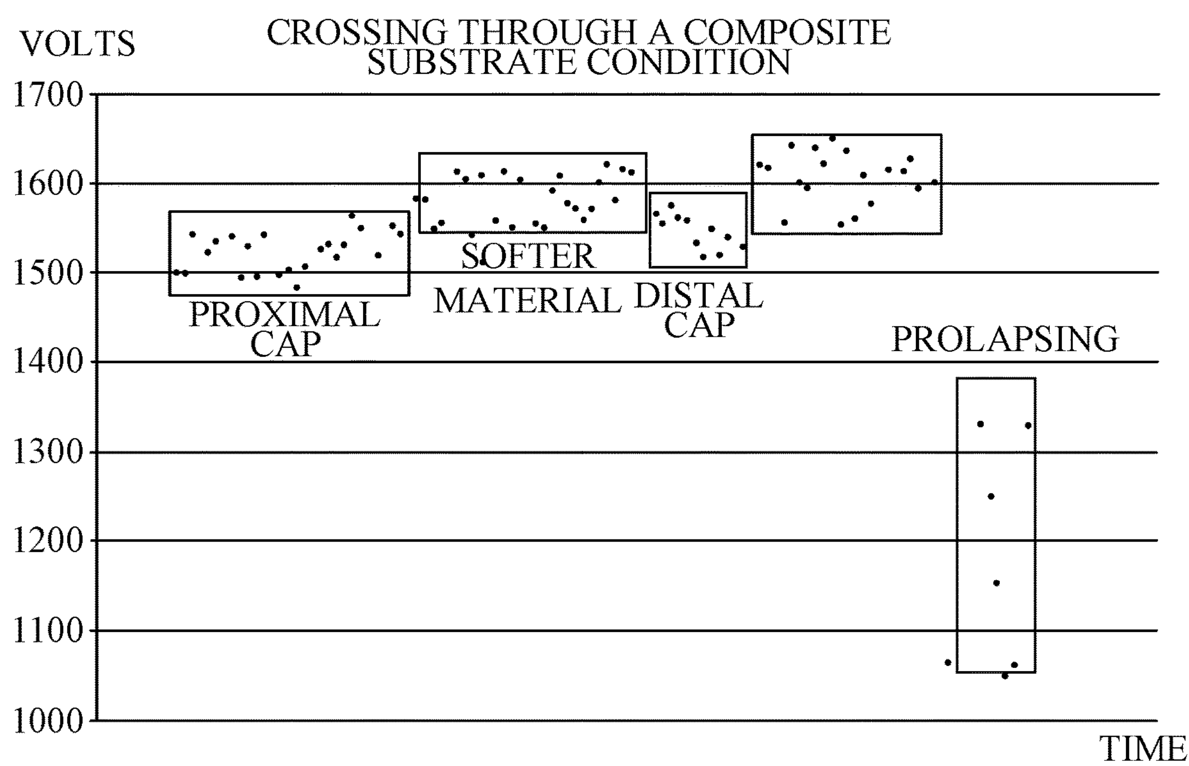
FIG. 6 is a graph that depicts a "crossing through a composite substrate" condition, for determining a threshold and/or data profile for use in detecting different types of substrates while traversing through the composite substrate.

The graph of FIG. 6 is directed to detecting different substrate types while traversing through a composited substrate in a vascular pathway, e.g., the composite substrate have a hard proximal and distal cap, and having a relatively softer material between the proximal cap and the distal cap. Empirical data was collected during normal running conditions, and during engagement and crossing of a composite substrate. The graph of FIG. 6 may form the basis for determining a threshold value (single point data), or alternatively profile data (multi-point data over time indicative of the condition), for comparison the digital representation of the total voltage signal S3, in real time, to detect a composite substrate, detect the engagement with the composite substrate and/or detect crossing of the composite substrate. The threshold, or alternatively the profile data, may be stored in memory circuit 20-5 for retrieval and use by processor circuit 20-1 in making the comparison, and for adjusting output control signal S4 if necessary to prevent prolapse.

For example, according to the graph of FIG. 6, a total voltage measured by voltage measuring circuit 18 below 1550 volts may be used as a total voltage threshold in a crossing state to indicate a transition of operation of ultrasonic treatment device 14 from a proximal cap to the softer interior material, and back to the distal cap. In this graph, a prolapse was detected below 1450. If the procedure remains above the total voltage threshold of 1550 for a predetermined amount of time, then the determination can be made that distal end 28-3 of ultrasonic vibration transmission member 28-2 is in the process of crossing the softer interior material between the proximal cap and the distal cap of the vascular occlusion.

Figure 7:
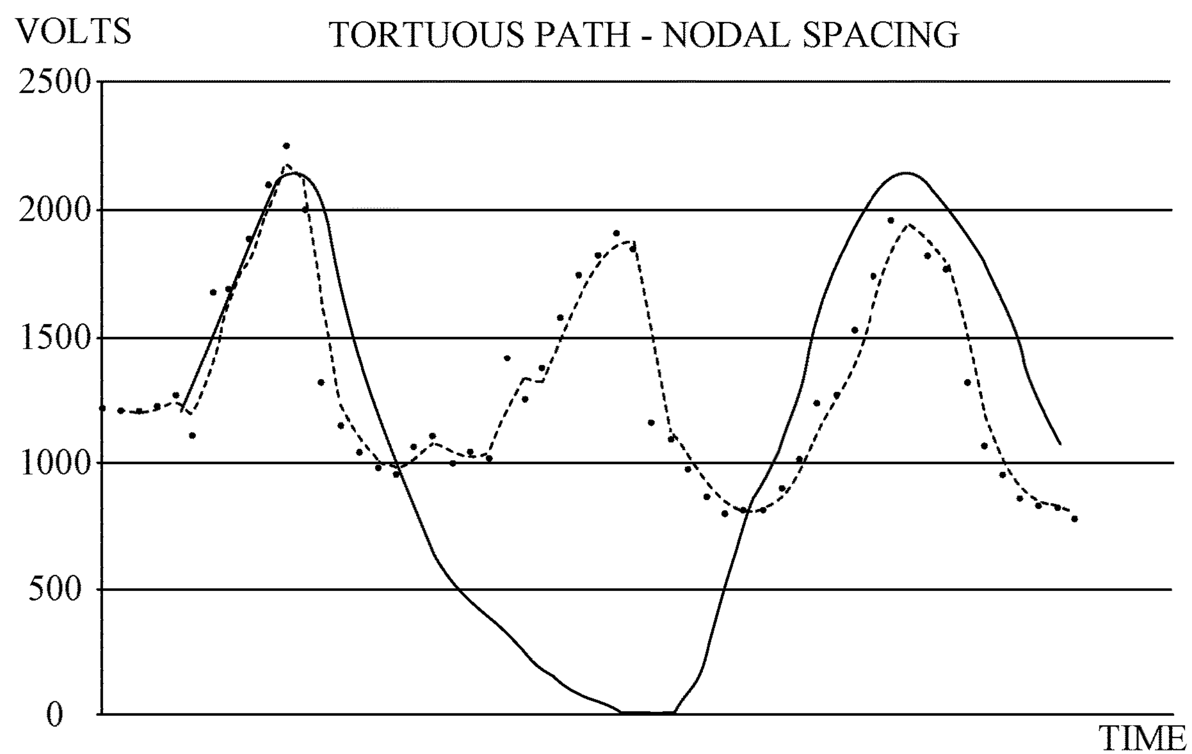
FIG. 7 is a graph that depicts a "tortuous path" condition for determining a threshold and/or data profile for use in detecting a tortuosity/performance variation through a bend in the vascular pathway.

FIG. 7 shows a graph that depicts a substantially sinusoidal variation of total voltage over time that is used for detecting tortuosity/performance variation through a bend in the vascular pathway. In this example, the graph shows an approximately sinusoidal variation of total voltage over time, wherein the time between the peaks of the sinusoid may be correlated to a nodal spacing of the ultrasonic vibration of ultrasonic vibration transmission member 28-2, e.g., 150 centimeters (cm), which is representative of tortuosity/performance variation through a bend in the vascular pathway. The graph of FIG. 7 may form the basis for determining a threshold value (single point data), or alternatively profile data (multi-point data over time indicative of the condition), for comparison the digital representation of the total voltage signal S3, in real time, to detect tortuosity/performance variation. The threshold, or alternatively the profile data, may be stored in memory circuit 20-5 for retrieval and use by processor circuit 20-1 in making the comparison.

While the graphs of FIGS. 3-7 were generated based on collection of data associated with monitoring the total voltage across ultrasonic transducer 24 for detecting various substrate materials, and prolapse and crossing conditions, in real time, those skilled in the art will recognize that similar empirical data may be collected and used in determining representative threshold values for detecting, in real time, prolapse and crossing events using any of the other electrical characteristics associated with ultrasonic transducer 24. In addition, it is contemplated that multiple electrical characteristics may be simultaneously monitored and used in real time detection of the various prolapse and crossing events. Thus, for example, the monitored electrical characteristic(s) may be one or more of the total voltage across ultrasonic transducer 24 as indicated by the digital representation of the total voltage signal S3, a total current to ultrasonic transducer 24 as indicated by the digital representation of the total current signal S2, an induced current of ultrasonic transducer 24 as calculated using the program instructions executed by processor circuit 20-1, and/or a Power Factor between the total voltage and the total current, as calculated using the program instructions executed by processor circuit 20-1.

The following items also relate to the invention:

In general, it is conceivable that a pathway is a pathway outside the human body. In one form, the invention relates to an ultrasonic system, optionally for vascular treatments, that includes an ultrasound signal generator configured to generate an ultrasound electrical signal. An ultrasonic treatment device is electrically coupled the ultrasound signal generator. The ultrasonic treatment device has an ultrasonic transducer drivably coupled to an ultrasonic vibration transmission member of an ultrasonic catheter. The ultrasonic transducer is configured to receive the ultrasound electrical signal to generate an ultrasonic vibratory motion of the ultrasonic vibration transmission member. Circuitry is configured to monitor an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current, the circuitry including a processor circuit configured to process the monitored electrical characteristic to determine at least one of a type of material encountered by a distal end of the ultrasonic vibration transmission member and a type of pathway (optionally a vascular pathway) that the ultrasonic catheter is traversing. The circuitry is configured to generate a control signal that is supplied to the ultrasound signal generator to control at least one of a modulation frequency and a waveform of the ultrasound electrical signal based on the determined at least one of the type material encountered by the distal end of the ultrasonic vibration transmission member and the type of pathway (optionally a vascular pathway) that the ultrasonic catheter is traversing.

A user interface may be included to display a result of the processing step at a display screen of a user interface. The result may include at least one of the type of material encountered by the distal end of the ultrasonic vibration transmission member, a prolapse condition, and the type of pathway (optionally a vascular pathway) that the ultrasonic catheter is traversing.

As set forth above, the act of monitoring may include monitoring a plurality of electrical characteristics associated with the ultrasonic transducer, the plurality of electrical characteristics including two or more of the total voltage across the ultrasonic transducer, the total current to the ultrasonic transducer, the induced current of the ultrasonic transducer, and the Power Factor between the total voltage and the total current. Also, the act of processing may include processing the monitored plurality of electrical characteristics to determine at least one of the material encountered by the distal end of the ultrasonic vibration transmission member and the type of pathway (optionally a vascular pathway) that the ultrasonic catheter is traversing.

The processor circuit may compare each monitored electrical characteristic to a respective threshold or data profile to determine the type of material encountered by the distal end of the ultrasonic vibration transmission member.

As a supplemental or alternative operation, the circuitry may be configured to monitor each monitored electrical characteristic to detect a change in value over time to determine a progress of advancement of the ultrasonic vibration transmission member through an obstruction (optionally a vascular obstruction) in the pathway (optionally a vascular pathway).

As a supplemental or alternative operation, the processor circuit may be configured to compare each monitored electrical characteristic to a respective threshold or data profile to determine the type of pathway (optionally a vascular pathway) that the ultrasonic catheter is traversing.

The invention also relates to a method for operating an ultrasonic treatment device in an ultrasonic system, the ultrasonic treatment device optionally being the device of paragraphs 54 to 59, the device having an ultrasonic transducer drivably coupled to an ultrasonic vibration transmission member of an ultrasonic catheter, including generating an ultrasound electrical signal using an ultrasound signal generator; supplying the ultrasound electrical signal to the ultrasonic transducer to generate ultrasonic vibratory motion of the ultrasonic vibration transmission member; monitoring an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current; processing the monitored electrical characteristic to determine at least one of a type of material encountered by a distal end of the ultrasonic vibration transmission member and a type of pathway that the ultrasonic catheter is traversing; and controlling at least one of a modulation frequency and a waveform of the ultrasound electrical signal based on the determined at least one of the type material encountered by the distal end of the ultrasonic vibration transmission member and the type of pathway that the ultrasonic catheter is traversing. The invention also refers to a system for applying such method and to a control unit for controlling a treatment device and/or ultrasonic system accordingly.

The method may also include displaying a result of the processing step at a display screen of a user interface, the result including at least one of the type of material encountered by the distal end of the ultrasonic vibration transmission member and the type of pathway that the ultrasonic catheter is traversing.

The step of monitoring may include monitoring a plurality of electrical characteristics associated with the ultrasonic transducer, the plurality of electrical characteristics including two or more of the total voltage across the ultrasonic transducer, the total current to the ultrasonic transducer, the induced current of the ultrasonic transducer, and the Power Factor between the total voltage and the total current.

The step of processing may include processing the monitored plurality of electrical characteristics to determine at least one of the material encountered by the distal end of the ultrasonic vibration transmission member and the type of pathway that the ultrasonic catheter is traversing.

The processing step may include comparing each monitored electrical characteristic to a respective threshold or data profile to determine the type of material encountered by the distal end of the ultrasonic vibration transmission member.

As a supplemental or alternative operation, the method may include monitoring each monitored electrical characteristic to detect a change in value over time to determine a progress of advancement of the ultrasonic vibration transmission member through an obstruction in the pathway.

As a supplemental or alternative operation, the processing step may include comparing each monitored electrical characteristic to a respective threshold or data profile to determine the type of pathway that the ultrasonic catheter is traversing.

The invention further relates to a method of determining an operational state of an ultrasonic treatment device, optionally the device of paragraphs 54 to 59, in an ultrasonic system, i.e. a method for operating an ultrasonic treatment device in an ultrasonic system, the ultrasonic treatment device having an ultrasonic transducer drivably coupled to an ultrasonic vibration transmission member of an ultrasonic catheter, including exciting the ultrasonic transducer with an ultrasound electrical signal using an ultrasound signal generator to generate ultrasonic vibratory motion of the ultrasonic vibration transmission member; monitoring an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current; processing the monitored electrical characteristic to determine at least one of a material encountered by a distal end of the ultrasonic vibration transmission member and a type of pathway that the ultrasonic catheter is traversing; and displaying a result of the processing step at a display screen of a user interface, the result including at least one of the type of material encountered by the distal end of the ultrasonic vibration transmission member and the type of pathway that the ultrasonic catheter is traversing. The invention also refers to a system for applying such method and to a control unit for controlling a treatment device and/or ultrasonic system accordingly.

The method may also include controlling at least one of a modulation frequency and a waveform of the ultrasound electrical signal based on the determined at least one of the material encountered by the distal end of the ultrasonic vibration transmission member and the type of pathway that the ultrasonic catheter is traversing.

The step of monitoring may include monitoring a plurality of electrical characteristics associated with the ultrasonic transducer, the plurality of electrical characteristics including two or more of the total voltage across the ultrasonic transducer, the total current to the ultrasonic transducer, the induced current of the ultrasonic transducer, and the Power Factor between the total voltage and the total current;

The step of processing may include determining from monitored plurality of electrical characteristics at least one of the type of material encountered by the distal end of the ultrasonic vibration transmission member and the type of pathway that the ultrasonic catheter is traversing.

The step of displaying may include displaying the result of the processing step at a display screen of a user interface that was based on the processing of the monitored plurality of electrical characteristics, the result including at least one of the type of material encountered by the distal end of the ultrasonic vibration transmission member and the type of pathway that the ultrasonic catheter is traversing.

The processing step may include comparing each monitored electrical characteristic to a respective threshold or data profile to determine the type of material encountered by the distal end of the ultrasonic vibration transmission member.

As a supplemental or alternative operation, the method may include monitoring at least one monitored electrical characteristic for a change in value over time to determine a progress of an advancement of the ultrasonic vibration transmission member through an obstruction in the pathway.

As a supplemental or alternative operation, the processing step may include comparing each monitored electrical characteristic to a respective threshold or data profile to determine the type of pathway that the ultrasonic catheter is traversing.

As used herein, the term “vascular pathway” may be either an actual vascular pathway in a being, e.g., animal or human, or may be a simulated representation of a vascular pathway, e.g., polymer tube(s) of various dimensions and configurations, wherein the ultrasonic system may be used for testing, evaluation, training, and/or treatment.

Also, as used herein, “substantially,”, “approximately”, and other words of degree are relative modifiers intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An ultrasonic system, comprising:

an ultrasound signal generator configured to generate an ultrasound electrical signal;

an ultrasonic treatment device electrically coupled the ultrasound signal generator, the ultrasonic treatment device having an ultrasonic transducer drivably coupled to an ultrasonic vibration transmission member of an ultrasonic catheter, the ultrasonic transducer receiving the ultrasound electrical signal to generate an ultrasonic vibratory motion of the ultrasonic vibration transmission member;

circuitry configured to monitor an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current, the circuitry including a processor circuit configured to process the monitored electrical characteristic to determine at least one of a type of material encountered by a distal end of the ultrasonic vibration transmission member and a type of vascular pathway that the ultrasonic catheter is traversing, the circuitry configured to generate a control signal that is supplied to the ultrasound signal generator to control at least one of a modulation frequency and a waveform of the ultrasound electrical signal based on the determined at least one of the type material encountered by the distal end of the ultrasonic vibration transmission member and the type of vascular pathway that the ultrasonic catheter is traversing.

2. The system of claim 1, comprising a user interface to display a result of the processing step at a display screen of a user interface, the result including at least one of the type of material encountered by the distal end of the ultrasonic vibration transmission member, a prolapse condition, and the type of vascular pathway that the ultrasonic catheter is traversing.

3. The system of claim 1, wherein:

the act of monitoring includes monitoring a plurality of electrical characteristics associated with the ultrasonic transducer, the plurality of electrical characteristics including two or more of the total voltage across the ultrasonic transducer, the total current to the ultrasonic transducer, the induced current of the ultrasonic transducer, and the Power Factor between the total voltage and the total current; and the act of processing includes processing the monitored plurality of electrical characteristics to determine at least one of the material encountered by the distal end of the ultrasonic vibration transmission member and the type of vascular pathway that the ultrasonic catheter is traversing.

4. The system of claim 1, wherein the processor circuit compares each monitored electrical characteristic to a respective threshold or data profile to determine the type of material encountered by the distal end of the ultrasonic vibration transmission member.

5. The system of claim 4, wherein the circuitry monitors each monitored electrical characteristic to detect a change in value over time to determine a progress of advancement of the ultrasonic vibration transmission member through a vascular obstruction in the vascular pathway.

6. The system of claim 1, wherein the processor circuit compares each monitored electrical characteristic to a respective threshold or data profile to determine the type of vascular pathway that the ultrasonic catheter is traversing.

7. A method for operating an ultrasonic treatment device in an ultrasonic system, the ultrasonic treatment device having an ultrasonic transducer drivably coupled to an ultrasonic vibration transmission member of an ultrasonic catheter, comprising:

generating an ultrasound electrical signal using an ultrasound signal generator;

supplying the ultrasound electrical signal to the ultrasonic transducer to generate ultrasonic vibratory motion of the ultrasonic vibration transmission member;

monitoring an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current;

processing the monitored electrical characteristic to determine at least one of a type of material encountered by a distal end of the ultrasonic vibration transmission member and a type of vascular pathway that the ultrasonic catheter is traversing; and controlling at least one of a modulation frequency and a waveform of the ultrasound electrical signal based on the determined at least one of the type material encountered by the distal end of the ultrasonic vibration transmission member and the type of vascular pathway that the ultrasonic catheter is traversing.

8. The method of claim 7, comprising displaying a result of the processing step at a display screen of a user interface, the result including at least one of the type of material encountered by the distal end of the ultrasonic vibration transmission member and the type of vascular pathway that the ultrasonic catheter is traversing.

9. The method of claim 7, wherein:

the step of monitoring includes monitoring a plurality of electrical characteristics associated with the ultrasonic transducer, the plurality of electrical characteristics including two or more of the total voltage across the ultrasonic transducer, the total current to the ultrasonic transducer, the induced current of the ultrasonic transducer, and the Power Factor between the total voltage and the total current; and the step of processing includes processing the monitored plurality of electrical characteristics to determine at least one of the material encountered by the distal end of the ultrasonic vibration transmission member and the type of vascular pathway that the ultrasonic catheter is traversing.

10. The method of claim 7, wherein the processing step includes comparing each monitored electrical characteristic to a respective threshold or data profile to determine the type of material encountered by the distal end of the ultrasonic vibration transmission member.

11. The method of claim 10, comprising monitoring each monitored electrical characteristic to detect a change in value over time to determine a progress of advancement of the ultrasonic vibration transmission member through a vascular obstruction in the vascular pathway.

12. The method of claim 7, wherein the processing step includes comparing each monitored electrical characteristic to a respective threshold or data profile to determine the type of vascular pathway that the ultrasonic catheter is traversing.

13. A method of determining an operational state of an ultrasonic treatment device in an ultrasonic system, the ultrasonic treatment device having an ultrasonic transducer drivably coupled to an ultrasonic vibration transmission member of an ultrasonic catheter, comprising:

exciting the ultrasonic transducer with an ultrasound electrical signal using an ultrasound signal generator to generate ultrasonic vibratory motion of the ultrasonic vibration transmission member;

monitoring an electrical characteristic associated with the ultrasonic transducer, the electrical characteristic being one of a total voltage across the ultrasonic transducer, a total current to the ultrasonic transducer, an induced current of the ultrasonic transducer, or a Power Factor between the total voltage and the total current;

processing the monitored electrical characteristic to determine at least one of a material encountered by a distal end of the ultrasonic vibration transmission member and a type of vascular pathway that the ultrasonic catheter is traversing; and displaying a result of the processing step at a display screen of a user interface, the result including at least one of the type of material encountered by the distal end of the ultrasonic vibration transmission member and the type of vascular pathway that the ultrasonic catheter is traversing.

14. The method of claim 13, comprising controlling at least one of a modulation frequency and a waveform of the ultrasound electrical signal based on the determined at least one of the material encountered by the distal end of the ultrasonic vibration transmission member and the type of vascular pathway that the ultrasonic catheter is traversing.

15. The method of claim 13, wherein:

the step of monitoring includes monitoring a plurality of electrical characteristics associated with the ultrasonic transducer, the plurality of electrical characteristics including two or more of the total voltage across the ultrasonic transducer, the total current to the ultrasonic transducer, the induced current of the ultrasonic transducer, and the Power Factor between the total voltage and the total current;

the step of processing includes determining from monitored plurality of electrical characteristics at least one of the type of material encountered by the distal end of the ultrasonic vibration transmission member and the type of vascular pathway that the ultrasonic catheter is traversing; and the step of displaying includes displaying the result of the processing step at a display screen of a user interface that was based on the processing of the monitored plurality of electrical characteristics, the result including at least one of the type of material encountered by the distal end of the ultrasonic vibration transmission member and the type of vascular pathway that the ultrasonic catheter is traversing.

16. The method of claim 13, wherein the processing step includes comparing each monitored electrical characteristic to a respective threshold or data profile to determine the type of material encountered by the distal end of the ultrasonic vibration transmission member.

17. The method of claim 16, comprising monitoring at least one monitored electrical characteristic for a change in value over time to determine a progress of an advancement of the ultrasonic vibration transmission member through a vascular obstruction in the vascular pathway.

18. The method of claim 13, wherein the processing step includes comparing each monitored electrical characteristic to a respective threshold or data profile to determine the type of vascular pathway that the ultrasonic catheter is traversing.

* * * * *